(12) United States Patent
Harrison et al.

(10) Patent No.: US 8,343,110 B2
(45) Date of Patent: Jan. 1, 2013

(54) INJECTION DEVICE

(75) Inventors: Nigel Harrison, Melbourn (GB); Rosemary Habeshaw, Melbourn (GB)

(73) Assignee: Cilag GmbH International (CH)

( * ) Notice: Subject to any disclaimer, the term of this patent is extended or adjusted under 35 U.S.C. 154(b) by 281 days.

(21) Appl. No.: 11/579,359

(22) PCT Filed: May 27, 2005

(86) PCT No.: PCT/GB2005/002135
§ 371 (c)(1),
(2), (4) Date: Aug. 28, 2008

(87) PCT Pub. No.: WO2005/115514
PCT Pub. Date: Dec. 8, 2005

(65) Prior Publication Data
US 2008/0312606 A1 Dec. 18, 2008

(30) Foreign Application Priority Data

| May 28, 2004 | (GB) | 0412048.1 |
| May 28, 2004 | (GB) | 0412049.9 |
| May 28, 2004 | (GB) | 0412050.7 |
| May 28, 2004 | (GB) | 0412051.5 |
| May 28, 2004 | (GB) | 0412053.1 |
| May 28, 2004 | (GB) | 0412054.9 |
| May 28, 2004 | (GB) | 0412055.6 |
| May 28, 2004 | (GB) | 0412056.4 |
| May 28, 2004 | (GB) | 0412057.2 |
| May 28, 2004 | (GB) | 0412061.9 |
| Apr. 6, 2005 | (GB) | 0507010.7 |

(51) Int. Cl.
*A61M 5/315* (2006.01)

(52) U.S. Cl. .................................................. 604/218
(58) Field of Classification Search ............. 604/218, 604/220, 219, 233, 235, 228
See application file for complete search history.

(56) References Cited

U.S. PATENT DOCUMENTS

| 1,845,036 A | 2/1932 | Busher |
| 2,019,382 A | 10/1935 | Aronson |

(Continued)

FOREIGN PATENT DOCUMENTS

CH 518102 A 1/1972

(Continued)

OTHER PUBLICATIONS

International Search Report dated Sep. 5,2005; International Application No. PCT/GB2005/002117.

(Continued)

*Primary Examiner* — Kevin C Sirmons
*Assistant Examiner* — Brandy C Scott

(57) ABSTRACT

A syringe is received within a housing, the syringe having a bore terminating at a forward end in a hypodermic needle and at a rearward end in a flared opening in which a bung having a bore surrounded by a skirt is insertod. A drive element has a forward end consisting of a substantially flat annular region that bears upon the skirt of the bung and surrounds a conical middle region that is received in the bore of the bung. An actuator advances the drive element so as to advance the bung and discharge the contents through the needle. The opening in the rear of the synnge is flared by being provided with a radius. The combination of the radius at the opening and the projecting conical middle region of the drive element allows misalignments of the two to be managed during automated assembly.

24 Claims, 4 Drawing Sheets

U.S. PATENT DOCUMENTS

| | | |
|---|---|---|
| 2,531,267 A | 11/1950 | Harisch |
| 2,764,977 A | 10/1956 | Ferguson |
| 2,828,742 A | 4/1958 | Ashkenaz |
| 3,329,146 A | 7/1967 | Waldman |
| 3,543,603 A | 12/1970 | Gley |
| 3,656,472 A | 4/1972 | Moura |
| 3,702,608 A | 11/1972 | Tibbs |
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,231,368 A | 11/1980 | Becker |
| 4,299,238 A | 11/1981 | Baidwan et al. |
| 4,378,015 A | 3/1983 | Wardlaw |
| 4,394,863 A | 7/1983 | Bartner |
| 4,407,283 A | 10/1983 | Reynolds |
| 4,425,120 A | 1/1984 | Sampson et al. |
| 4,430,082 A | 2/1984 | Schwabacher |
| 4,521,237 A | 6/1985 | Logothetis |
| 4,561,856 A | 12/1985 | Cochran |
| 4,636,201 A | 1/1987 | Ambrose et al. |
| 4,744,786 A | 5/1988 | Hooven |
| 4,787,891 A | 11/1988 | Levin et al. |
| 4,874,383 A | 10/1989 | McNaughton |
| 4,929,232 A | 5/1990 | Sweeney et al. |
| 4,988,339 A | 1/1991 | Vadher |
| 5,009,646 A | 4/1991 | Sudo et al. |
| 5,026,349 A | 6/1991 | Schmitz et al. |
| 5,057,079 A | 10/1991 | Tiemann et al. |
| 5,092,842 A | 3/1992 | Bechtold et al. |
| 5,098,400 A | 3/1992 | Crouse et al. |
| 5,114,406 A | 5/1992 | Gabriel et al. |
| 5,122,119 A | 6/1992 | Lucas |
| 5,137,516 A | 8/1992 | Rand et al. |
| 5,141,496 A | 8/1992 | Dalto et al. |
| 5,156,599 A | 10/1992 | Ranford et al. |
| 5,176,643 A | 1/1993 | Kramer et al. |
| 5,190,526 A | 3/1993 | Murray et al. |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,330,430 A | 7/1994 | Sullivan |
| 5,358,489 A | 10/1994 | Wyrick |
| 5,372,586 A | 12/1994 | Haber et al. |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,514,097 A | 5/1996 | Knauer |
| 5,520,653 A | 5/1996 | Reilly et al. |
| 5,540,660 A | 7/1996 | Jenson |
| 5,540,709 A | 7/1996 | Ramel |
| 5,567,160 A | 10/1996 | Massino |
| 5,569,192 A | 10/1996 | van der Wal |
| 5,575,777 A | 11/1996 | Cover et al. |
| 5,599,302 A | 2/1997 | Lilley et al. |
| 5,599,309 A | 2/1997 | Marshall et al. |
| 5,609,577 A | 3/1997 | Haber et al. |
| 5,609,584 A | 3/1997 | Gettig et al. |
| 5,637,094 A | 6/1997 | Stewart, Jr. et al. |
| 5,645,536 A | 7/1997 | Whisson |
| 5,647,845 A | 7/1997 | Haber et al. |
| 5,665,071 A | 9/1997 | Wyrick |
| 5,681,291 A | 10/1997 | Galli |
| 5,697,908 A | 12/1997 | Imbert et al. |
| 5,702,367 A | 12/1997 | Cover et al. |
| 5,704,911 A | 1/1998 | Parsons |
| 5,709,662 A | 1/1998 | Olive et al. |
| 5,779,668 A * | 7/1998 | Grabenkort ............... 604/89 |
| 5,779,677 A | 7/1998 | Frezza |
| 5,807,334 A | 9/1998 | Hodosh et al. |
| 5,817,058 A | 10/1998 | Shaw |
| 5,843,036 A | 12/1998 | Olive et al. |
| 5,868,711 A | 2/1999 | Kramer et al. |
| 5,879,327 A | 3/1999 | Moreau DeFarges et al. |
| 5,913,843 A | 6/1999 | Jentzen |
| 5,928,205 A | 7/1999 | Marshall |
| 5,954,738 A | 9/1999 | LeVaughn et al. |
| 5,957,897 A | 9/1999 | Jeffrey |
| 5,960,797 A | 10/1999 | Kramer et al. |
| 5,997,513 A | 12/1999 | Smith et al. |
| 6,015,438 A | 1/2000 | Shaw |
| 6,017,330 A * | 1/2000 | Hitchins et al. ............... 604/218 |
| 6,036,675 A | 3/2000 | Thorne et al. |
| 6,045,534 A | 4/2000 | Jacobsen et al. |
| 6,068,614 A | 5/2000 | Kimber et al. |
| 6,077,247 A | 6/2000 | Marshall et al. |
| 6,083,197 A | 7/2000 | Umbaugh |
| 6,086,562 A | 7/2000 | Jacobsen et al. |
| 6,090,070 A | 7/2000 | Hager et al. |
| 6,090,078 A | 7/2000 | Erskine |
| 6,090,897 A | 7/2000 | Akasaki et al. |
| 6,099,503 A | 8/2000 | Stradella |
| 6,099,504 A | 8/2000 | Gross et al. |
| 6,159,181 A | 12/2000 | Crossman et al. |
| 6,162,199 A | 12/2000 | Geringer |
| 6,171,276 B1 | 1/2001 | Markus et al. |
| 6,179,812 B1 | 1/2001 | Botich et al. |
| 6,186,980 B1 | 2/2001 | Brunel |
| 6,190,363 B1 | 2/2001 | Gabbard et al. |
| 6,193,696 B1 | 2/2001 | Jansen et al. |
| 6,203,530 B1 | 3/2001 | Stewart, Sr. |
| 6,221,044 B1 | 4/2001 | Greco |
| 6,258,068 B1 | 7/2001 | Kirchhofer et al. |
| 6,270,479 B1 | 8/2001 | Bergens et al. |
| 6,280,421 B1 | 8/2001 | Kirchhofer et al. |
| 6,293,925 B1 | 9/2001 | Safabash et al. |
| 6,371,939 B2 | 4/2002 | Bergens et al. |
| 6,371,959 B1 | 4/2002 | Trice |
| 6,387,078 B1 | 5/2002 | Gillespie, III |
| 6,391,003 B1 | 5/2002 | Lesch, Jr. |
| 6,419,658 B1 | 7/2002 | Restelli et al. |
| 6,428,528 B2 | 8/2002 | Sadowski et al. |
| 6,447,480 B1 | 9/2002 | Brunel |
| 6,454,743 B1 | 9/2002 | Weber |
| 6,454,746 B1 | 9/2002 | Bydion et al. |
| 6,461,333 B1 | 10/2002 | Frezza |
| 6,517,517 B1 | 2/2003 | Farrugia et al. |
| 6,537,252 B1 | 3/2003 | Hansen |
| 6,544,234 B1 | 4/2003 | Gabriel |
| 6,565,540 B1 | 5/2003 | Perouse et al. |
| 6,565,553 B2 | 5/2003 | Sadowski et al. |
| 6,569,115 B1 | 5/2003 | Barker et al. |
| 6,569,123 B2 | 5/2003 | Alchas et al. |
| 6,569,124 B1 | 5/2003 | Perouse |
| 6,572,581 B1 | 6/2003 | Landau |
| 6,575,939 B1 | 6/2003 | Brunel |
| 6,585,702 B1 | 7/2003 | Brunel |
| 6,589,210 B1 | 7/2003 | Rolfe |
| 6,595,957 B1 | 7/2003 | Griffiths et al. |
| 6,595,962 B1 | 7/2003 | Perthu |
| 6,607,508 B2 | 8/2003 | Knauer |
| 6,607,510 B2 | 8/2003 | Landau |
| 6,613,022 B1 | 9/2003 | Doyle |
| 6,620,137 B2 | 9/2003 | Kirchhofer et al. |
| 6,638,256 B2 | 10/2003 | Jansen et al. |
| 6,641,554 B2 | 11/2003 | Landau |
| 6,641,560 B1 | 11/2003 | Bechtold et al. |
| 6,641,565 B1 | 11/2003 | Lavi et al. |
| 6,645,170 B2 | 11/2003 | Landau |
| 6,645,181 B1 | 11/2003 | Lavi et al. |
| 6,648,835 B1 | 11/2003 | Shemesh |
| 6,648,850 B2 | 11/2003 | Landau |
| 6,656,163 B1 | 12/2003 | Marshall et al. |

| | | |
|---|---|---|
| 6,673,049 B2 | 1/2004 | Hommann et al. |
| 6,676,630 B2 | 1/2004 | Landau et al. |
| 6,689,093 B2 | 2/2004 | Landau |
| 6,692,469 B1 | 2/2004 | Weekes et al. |
| 6,699,220 B2 | 3/2004 | Rolfe |
| 6,740,062 B2 | 5/2004 | Hjertman |
| 6,743,199 B2 | 6/2004 | Shue et al. |
| 6,743,203 B1 | 6/2004 | Pickhard |
| 6,746,429 B2 | 6/2004 | Sadowski et al. |
| 6,767,336 B1 | 7/2004 | Kaplan |
| 6,770,056 B2 | 8/2004 | Price et al. |
| 6,776,777 B2 | 8/2004 | Barrelle |
| 6,783,509 B1 | 8/2004 | Landau et al. |
| 6,793,161 B1 | 9/2004 | Fujita et al. |
| 6,796,967 B2 | 9/2004 | Jensen |
| 6,811,548 B2 | 11/2004 | Jeffrey |
| 6,846,303 B2 | 1/2005 | Eakins et al. |
| 6,890,319 B1 | 5/2005 | Crocker |
| 6,899,698 B2 | 5/2005 | Sams |
| 6,932,793 B1 | 8/2005 | Marshall et al. |
| 6,939,319 B1 | 9/2005 | Anstead et al. |
| 6,979,316 B1 | 12/2005 | Rubin et al. |
| 7,066,907 B2 | 6/2006 | Crossman et al. |
| 7,097,634 B2 | 8/2006 | Gilbert |
| 7,118,553 B2 | 10/2006 | Scherer |
| 7,156,823 B2 | 1/2007 | Landau et al. |
| 7,744,561 B2 | 6/2010 | Stamp |
| 2001/0005781 A1 | 6/2001 | Bergens et al. |
| 2001/0021828 A1 | 9/2001 | Fischer et al. |
| 2001/0037087 A1 | 11/2001 | Knauer |
| 2001/0037089 A1 | 11/2001 | Domici, Jr. |
| 2001/0049496 A1 | 12/2001 | Kirchhofer et al. |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0173752 A1 | 11/2002 | Polzin |
| 2002/0183690 A1 | 12/2002 | Arnisolle |
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sharpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0233070 A1 | 12/2003 | De La Serna et al. |
| 2003/0236502 A1 | 12/2003 | De La Serna et al. |
| 2003/0236504 A1 | 12/2003 | Chen |
| 2004/0015134 A1 | 1/2004 | Lavi et al. |
| 2004/0019326 A1 | 1/2004 | Gilbert et al. |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0124940 A1 | 6/2005 | Martin et al. |
| 2005/0125019 A1 | 6/2005 | Kudrna et al. |
| 2005/0137523 A1 | 6/2005 | Wyatt et al. |
| 2005/0203466 A1 | 9/2005 | Hommann et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1* | 3/2006 | Parker et al. ............ 604/110 |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178631 A1 | 8/2006 | Gillespie et al. |
| 2006/0178642 A1 | 8/2006 | Gillespie et al. |
| 2006/0184137 A1 | 8/2006 | Reynolds |
| 2006/0224124 A1 | 10/2006 | Scherer |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0078382 A1 | 4/2007 | Hommann et al. |
| 2007/0142787 A1 | 6/2007 | Scherer |
| 2008/0312606 A1 | 12/2008 | Harrison et al. |
| 2009/0054849 A1 | 2/2009 | Burnell et al. |
| 2009/0088688 A1 | 4/2009 | Timothy Donald et al. |
| 2010/0016793 A1 | 1/2010 | Jennings et al. |

FOREIGN PATENT DOCUMENTS

| | | |
|---|---|---|
| CN | 2059579 U | 7/1990 |
| CN | 1190599 A | 8/1998 |
| CN | 1541121 A | 10/2004 |
| CN | 1550240 A | 12/2004 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 1/1997 |
| DE | 69506521 T2 | 6/1999 |
| DE | 10137962 A1 | 2/2003 |
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0331452 A2 | 8/1993 |
| EP | 0585626 A1 | 3/1994 |
| EP | 0389938 B1 | 5/1994 |
| EP | 0482677 B1 | 4/1998 |
| EP | 0602883 B1 | 7/1998 |
| EP | 0857491 A1 | 8/1998 |

| | | | | | | |
|---|---|---|---|---|---|---|
| EP | 0824922 | B1 | 4/2002 | JP | 2003-511105 T | 3/2003 |
| EP | 1260241 | A1 | 11/2002 | JP | 2003-532500 T | 11/2003 |
| EP | 0824923 | B1 | 7/2003 | JP | 2003-533288 A | 11/2003 |
| EP | 1228777 | B1 | 10/2003 | JP | 2004-533282 T | 11/2004 |
| EP | 0991441 | B1 | 12/2003 | JP | 2004-33737 A | 8/2005 |
| EP | 1166809 | B1 | 3/2004 | NZ | 573171 A | 11/2010 |
| EP | 0666084 | B1 | 4/2004 | NZ | 573350 A | 12/2010 |
| EP | 0941133 | B1 | 4/2004 | WO | WO 88/10129 A1 | 12/1988 |
| EP | 1124601 | B1 | 12/2004 | WO | WO 98/10129 A1 | 12/1988 |
| EP | 1364667 | B1 | 4/2005 | WO | WO 92/19296 A | 11/1992 |
| EP | 1208858 | B1 | 6/2006 | WO | WO 93/02186 A1 | 2/1993 |
| EP | 1755710 | A1 | 2/2007 | WO | WO 93/21986 A2 | 11/1993 |
| EP | 1586341 | B1 | 1/2008 | WO | WO 93/23098 A1 | 11/1993 |
| EP | 1932558 | A1 | 6/2008 | WO | WO 94/04207 A1 | 3/1994 |
| EP | 2023980 | A1 | 2/2009 | WO | WO 94/07554 A1 | 4/1994 |
| EP | 2129414 | A1 | 12/2009 | WO | WO 94/11041 | 5/1994 |
| EP | 1755706 | B1 | 3/2010 | WO | WO 94/13342 A1 | 6/1994 |
| EP | 1928523 | B1 | 7/2010 | WO | WO 94/21316 A1 | 9/1994 |
| EP | 1518575 | B1 | 11/2010 | WO | WO 94/22511 A1 | 10/1994 |
| FR | 1014881 | A | 8/1952 | WO | WO 95/04562 A1 | 2/1995 |
| FR | 1169935 | A | 1/1959 | WO | WO 95/29720 A1 | 11/1995 |
| FR | 1538565 | A | 9/1968 | WO | WO 95/31235 A1 | 11/1995 |
| FR | 2506161 | A1 | 11/1982 | WO | WO 95/35126 A1 | 11/1995 |
| FR | 2629706 | A | 10/1989 | WO | WO 95/35126 A1 | 12/1995 |
| FR | 2654938 | A1 | 5/1991 | WO | WO 96/30265 A1 | 10/1996 |
| FR | 2665079 | A1 | 1/1992 | WO | WO 97/10865 A1 | 3/1997 |
| FR | 2717086 | A1 | 9/1995 | WO | WO 97/13538 A1 | 4/1997 |
| FR | 2741810 | A1 | 6/1997 | WO | WO 97/48430 A1 | 12/1997 |
| FR | 2861310 | A1 | 4/2005 | WO | WO 98/11927 A1 | 3/1998 |
| GB | 143084 | | 5/1920 | WO | WO 99/03529 A2 | 1/1999 |
| GB | 0412054 | | 6/1934 | WO | WO 99/10030 A2 | 3/1999 |
| GB | 728248 | | 4/1955 | WO | WO 99/22789 A1 | 5/1999 |
| GB | 909898 | | 11/1962 | WO | WO 99/37343 A | 7/1999 |
| GB | 1263355 | | 2/1972 | WO | WO 99/53979 A1 | 10/1999 |
| GB | 1311937 | A | 3/1973 | WO | WO 99/59658 A1 | 11/1999 |
| GB | 1514725 | | 6/1978 | WO | WO 00/06227 A1 | 2/2000 |
| GB | 2338033 | A | 12/1999 | WO | WO 00/07539 A1 | 2/2000 |
| GB | 2388033 | A | 11/2003 | WO | WO 00/13723 A2 | 3/2000 |
| GB | 2396298 | A | 6/2004 | WO | WO 00/24441 A1 | 5/2000 |
| GB | 2396816 | A | 7/2004 | WO | WO 00/35516 | 6/2000 |
| GB | 2397767 | A | 8/2004 | WO | WO 00/50107 A1 | 8/2000 |
| GB | 2414398 | A | 11/2005 | WO | WO 00/64515 A1 | 11/2000 |
| GB | 2414399 | A | 11/2005 | WO | WO 00/69488 A2 | 11/2000 |
| GB | 2414400 | A | 11/2005 | WO | WO 01/05456 A1 | 1/2001 |
| GB | 2414401 | A | 11/2005 | WO | WO 01/49347 A1 | 7/2001 |
| GB | 2414402 | A | 11/2005 | WO | WO 01/76666 A1 | 10/2001 |
| GB | 2414403 | A | 11/2005 | WO | WO 01/87384 A1 | 11/2001 |
| GB | 2424835 | A | 10/2006 | WO | WO 02/11799 A1 | 2/2002 |
| GB | 2424836 | A | 10/2006 | WO | WO 02/47746 A1 | 6/2002 |
| GB | 2424838 | A | 10/2006 | WO | WO 02/056947 A1 | 7/2002 |
| GB | 2433035 | A | 6/2007 | WO | WO 03/013632 A2 | 2/2003 |
| GB | 2437922 | A | 11/2007 | WO | WO 03/015853 A1 | 2/2003 |
| GB | 2438591 | A | 12/2007 | WO | WO 03/039633 A2 | 5/2003 |
| GB | 2446778 | A | 8/2008 | WO | WO 03/041768 A | 5/2003 |
| JP | 59-115053 | A | 7/1984 | WO | WO 03/047663 A2 | 6/2003 |
| JP | 2-185261 | A | 7/1990 | WO | WO 03/051434 A2 | 6/2003 |
| JP | 2-502971 | T | 9/1990 | WO | WO 03/066141 A1 | 8/2003 |
| JP | 11-501549 | T | 2/1992 | WO | WO 03/092771 | 11/2003 |
| JP | 5-161712 | A | 6/1993 | WO | WO 03/097133 | 11/2003 |
| JP | 6-209996 | A | 8/1994 | WO | WO 03/099358 A2 | 12/2003 |
| JP | 6-508773 | T | 10/1994 | WO | WO 2004/007554 A1 | 1/2004 |
| JP | 6-327770 | A | 11/1994 | WO | WO 04/011065 A | 2/2004 |
| JP | 7-222799 | A | 8/1995 | WO | WO 2004/030732 A2 | 4/2004 |
| JP | 8-502180 | T | 3/1996 | WO | WO 2004/035117 A2 | 4/2004 |
| JP | 8-504354 | T | 5/1996 | WO | WO 2004/047890 A1 | 6/2004 |
| JP | 9-225029 | A | 9/1997 | WO | WO 2004/047891 A1 | 6/2004 |
| JP | 10-504474 | T | 5/1998 | WO | WO 2004/047892 A | 6/2004 |
| JP | 10-507935 | A | 8/1998 | WO | WO 2004/054644 A1 | 7/2004 |
| JP | 11-503637 | T | 3/1999 | WO | WO 2004/054645 A3 | 7/2004 |
| JP | 11-504536 | T | 4/1999 | WO | WO 2004/087242 A1 | 10/2004 |
| JP | 11-164887 | T | 6/1999 | WO | WO 2004/108194 A1 | 12/2004 |
| JP | 11-512332 | T | 10/1999 | WO | WO 2005/009515 A1 | 2/2005 |
| JP | 2000-510021 | T | 8/2000 | WO | WO 2005/023341 A1 | 3/2005 |
| JP | 2002-500933 | T | 1/2002 | WO | WO 2005/025636 A2 | 3/2005 |
| JP | 2002-095749 | A | 4/2002 | WO | WO 2005/030301 A1 | 4/2005 |
| JP | 2002-513547 | T | 5/2002 | WO | WO 2005/035028 A1 | 4/2005 |
| JP | 2002-526175 | A | 8/2002 | WO | WO 2005/044345 A | 5/2005 |
| JP | 2002-528182 | T | 9/2002 | WO | WO 2005/044347 A1 | 5/2005 |
| JP | 2002-532161 | T | 10/2002 | WO | WO 2005/058396 A1 | 6/2005 |

| | | | |
|---|---|---|---|
| WO | WO 2005/070481 A1 | 8/2005 |
| WO | WO 2005/082438 A1 | 9/2005 |
| WO | WO 2005/097238 A3 | 10/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/120607 A2 | 12/2005 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | WO 2007/122193 A1 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/075033 A | 6/2008 |
| WO | WO 2008/093063 A2 | 8/2008 |
| WO | WO 88/08725 | 11/2008 |

OTHER PUBLICATIONS

International Search Report dated May 30, 2006; International Application No. PCT/GB2005/003725.
International Search Report dated Sep. 9, 2005; International Application No. PCT/GB2005/002126.
Australian Search Report dated Dec. 6, 2007; Application No. SG 200608164-0.
International Search Report dated Sep. 5, 2005; International Application No. PCT/GB2005/002131.
Austrian Search Report dated Jan. 22, 2006; Application No. 200608166-5.
International Search Report dated Sep. 9, 2005; International Application No. PCT/GB2005/002120.
International Search Report dated Sep. 6, 2005; International Application No. PCT/GB2005/002108.
European Search Report dated Apr. 23, 2007; Application No. 06077332.2.
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.
Australian Search Report dated Dec. 11, 2007; Application No. 200608165-7.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/1132006/002792.
European Search Report dated Feb. 1, 2006; Application No. 05255298.1.
Great Britain Search Report dated Sep. 22, 2006; Application No. GB0610860.9.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2.
International Search Report dated Oct. 14, 2008; International Application No. PCT/GB2008/002580.
Great Britain Search Report dated Nov. 12, 2007; Application No. GB0715459.4.
International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.
Great Britain Search Report dated Nov. 12, 2007; Application No. GB0715456.0.
International Search Report dated Oct. 10, 2008; International Application No. PCT/GB2008/002583.
Great Britain Search Report dated Nov. 12, 2007; Application No. GB0715457.8.
International Search Report dated Sep. 30, 2009; International Application No. PCT/GB2009/001447.
Great Britain Search Report dated Sep. 25, 2008; Application No. GB0811348.2.
International Search Report dated Oct. 2, 2009; International Application No. PCT/GB2009/001448.
Great Britain Search Report dated Sep. 25, 2008; Application No. GB0811346.6.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.
International Search Report dated Oct. 5, 2009; International Application No. PCT/GB2009/001445.
Great Britain Search Report dated Sep. 25, 2008; Application No. GB0811349.0.
International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.

* cited by examiner

INJECTION DEVICE

BACKGROUND TECHNOLOGY

The present invention is concerned with injection devices of the type that include a housing, a syringe received within the housing, the syringe having a bore in which a discharge piston having a bore is inserted, a drive element and an actuator for advancing the drive element so as to advance the discharge piston and discharge the contents of the syringe through its discharge nozzle.

These days, nearly everything is manufactured by machines. In some circumstances, machines are more reliable that manual labour and are they are very much less expensive. However, there is one faculty of a production line worker that, hitherto, machines have been unable to reproduce, and are unlikely to be able to do so for a long time to come. If a production line worker drops a part of the thing being manufactured, he may pick it up or he may select another from the parts bin. If a part is damaged, he may discard it. If the assembly operation he is undertaking is complex, he will ensure that the parts are properly aligned and assembled. He does all of these things because he is able to adapt to different circumstances and to use his judgment. Machines cannot.

During automated assembling of injection devices of the type mentioned above, there are a number of critical steps that need to be performed accurately and properly. Difficulties in performing these steps may arise from tight component tolerances or from the use of fragile components, such as glass hypodermic syringes. The particular assembly step with which the present invention is concerned is that of getting the drive element into the bore of the syringe, to which a number of challenges attach. Firstly, to act on the outer diameter of the syringe piston, it is necessary for the drive element to have a flat end face that is a close fit in the syringe bore. Secondly, this flat end face presents the risk that the drive element may jam onto the end of the syringe, particularly if there is any misalignment between the components. Thirdly, if automation is used to assemble the devices a jam between the drive element and the syringe could result in damage to the device or even breakage of the syringe. Finally, even if this operation is done by hand, it is often necessary to do it blind.

SUMMARY OF THE INVENTION

It is an object of the present invention to provide a construction of injection device in which possible misalignment between the drive element and the syringe bore during assembly is already accounted for and does not so easily lead to a jam between the drive element and the syringe.
Accordingly, an injection device according to the present invention comprises:
  a housing;
  a syringe received within the housing, the syringe having a bore terminating at a forward end in a discharge nozzle and at a rearward end in a flared opening in which a discharge piston having a bore is inserted;
  a drive element having a forward end consisting of a substantially flat edge region that is adapted to bear upon the discharge piston of the syringe and surrounds a projecting middle region that is adapted to be received in the bore of the discharge piston; and
  an actuator for advancing the drive element so as to advance the discharge piston and discharge the contents of the syringe through the discharge nozzle.

The combination of the flared opening to the syringe bore and the projecting middle region of the drive element allows the problems associated with mild misalignments of the two to be overcome. This is because the projecting middle region either passes straight into the end of the syringe, or it contacts the flared opening which guides it towards the centre of the syringe. Coupled with force sensors on the assembly machines, this arrangement will allow the appropriate automatic adjustment to be made to the alignment of the two parts.

Alternatively, and this is thought to be better because it does not rely on force sensors or other sophisticated modifications of the assembly machines, any misalignment is automatically corrected in full. This can be achieved if the flared opening in the syringe and the substantially flat edge and projecting middle regions of the forward end of the drive element are so shaped and dimensioned that axial misalignment between the syringe and the drive element during assembly of the injection device are corrected by, firstly, the projecting middle region of the forward end of the drive element riding up the flared opening of the syringe to a point at which, secondly, the substantially flat edge region of the forward end of the drive element makes contact with and rides up the flared opening of the syringe to align the drive element in the bore of the syringe.

The appropriate amount of flaring of the opening will depend upon a number of variables. Take a line formed by the intersection of the flared opening of the syringe and a plane that passes through the axis of the syringe bore. Preferably, this line possesses a radius of curvature of between 33% and 100% of the radius of the syringe bore. In the preferred embodiment, it possesses a radius of curvature of between 1 mm and 3 mm. This radius of curvature may be an instantaneous radius of curvature; it may be an average radius of curvature; it may be a minimum radius of curvature.

In embodiments in which the shape and dimensions of the flared opening in the syringe and the substantially flat edge and projecting middle regions of the forward end of the drive element are designed to correct axial misalignment in full, this radius of curvature should preferably be greater than the maximum radial extent of the substantially flat edge region of the forward end of the drive element. Better results are obtained if it is at least 50% greater than the maximum radial extent of the substantially flat edge region of the forward end of the drive element. Even better results follow if it is at least 70% greater.

To allow all directions of axial misalignment to be dealt with equally, the flared opening of the syringe is preferably substantially a surface of revolution about the axis of the syringe bore.

The present invention also extends to an injection device comprising:
  a housing adapted to receive a syringe having a bore terminating at a forward end in a discharge nozzle and at a rearward end in a flared opening in which a discharge piston having a bore is inserted; and
  a drive element that is adapted to bear upon the discharge piston of the syringe; and
  an actuator for advancing the drive element so as to advance the discharge piston and discharge the contents of the syringe through the discharge nozzle, the forward end of the drive element consisting of a substantially flat edge region surrounding a projecting middle region.

Normally, the forward end of the drive element has a cross-sectional area in the range 6.5 mm$^2$ to 110 mm$^2$, preferably 27.3 mm$^2$±8%.

Again, to allow all directions of axial misalignment to be dealt with equally, the forward end of the drive element may be substantially circular in cross-section. In that case, the forward end of the drive element normally has a radius in the range 1.45 mm to 5.9 mm, preferably 2.95 mm±4%.

The substantially flat edge region of the forward end of the drive element may account for between 25% and 50% of the total area of the forward end of the drive element, preferably 37±3% of the total area of the forward end of the drive element.

Again, to allow all directions of axial misalignment to be dealt with equally, the substantially flat edge region of the forward end of the drive element may be substantially annular. Preferably, the inner diameter of the substantially flat annular region is 61±2% of the outer diameter.

Again, to allow all directions of axial misalignment to be dealt with equally, the projecting middle region of the forward end of the drive element is substantially circular in shape. For reasons that will be obvious, the projecting middle region of the forward end of the drive element preferably tapers from the substantially flat edge region to a neb. It is thought that best results may be obtained if the projecting middle region of the forward end of the drive element tapers at an average angle of between 35±10° to the longitudinal axis of the drive element. For example, the projecting middle region of the forward end of the drive element may be substantially conical or frustoconical with an included cone angle of 65±5°.

BRIEF DESCRIPTION OF THE DRAWINGS

The present invention will now be describe by way of example with reference to the accompanying drawings, in which.

DETAILED DESCRIPTION OF THE PREFERRED EMBODIMENTS

Figure 1:
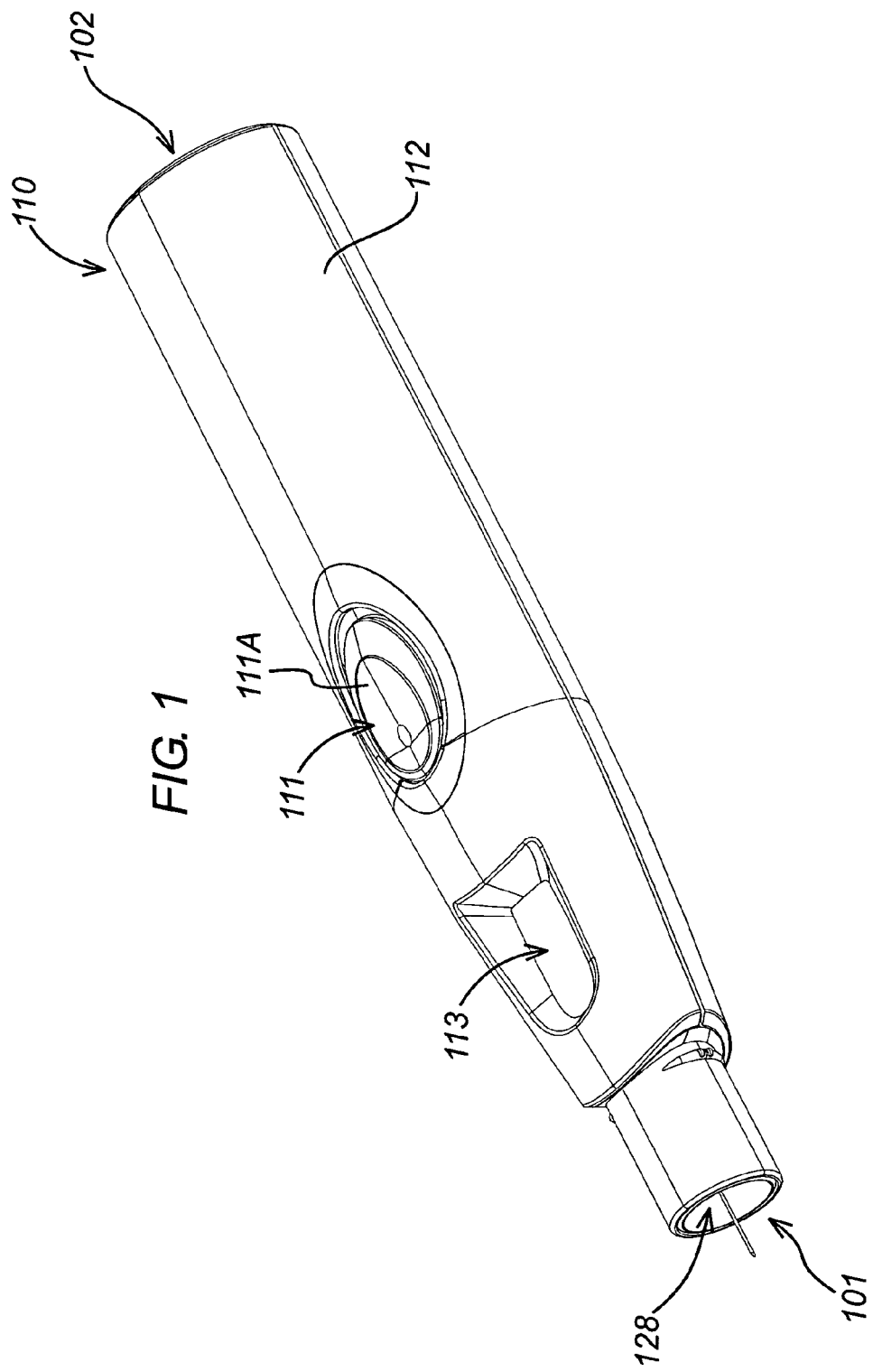
FIG. 1 shows in perspective an injection device of the type to which the present invention is applicable.

FIG. 1 shows an injection device 110 having a housing 112 with a proximal end 101 and a distal end 102. All parts are injection-moulded. The housing 112 has a trigger 111 which projects through the housing 112 and which can be actuated by pressing down on its upper surface 111a. There is a indicator opening 113 in the housing located adjacent the proximal end 101.

Figure 2:
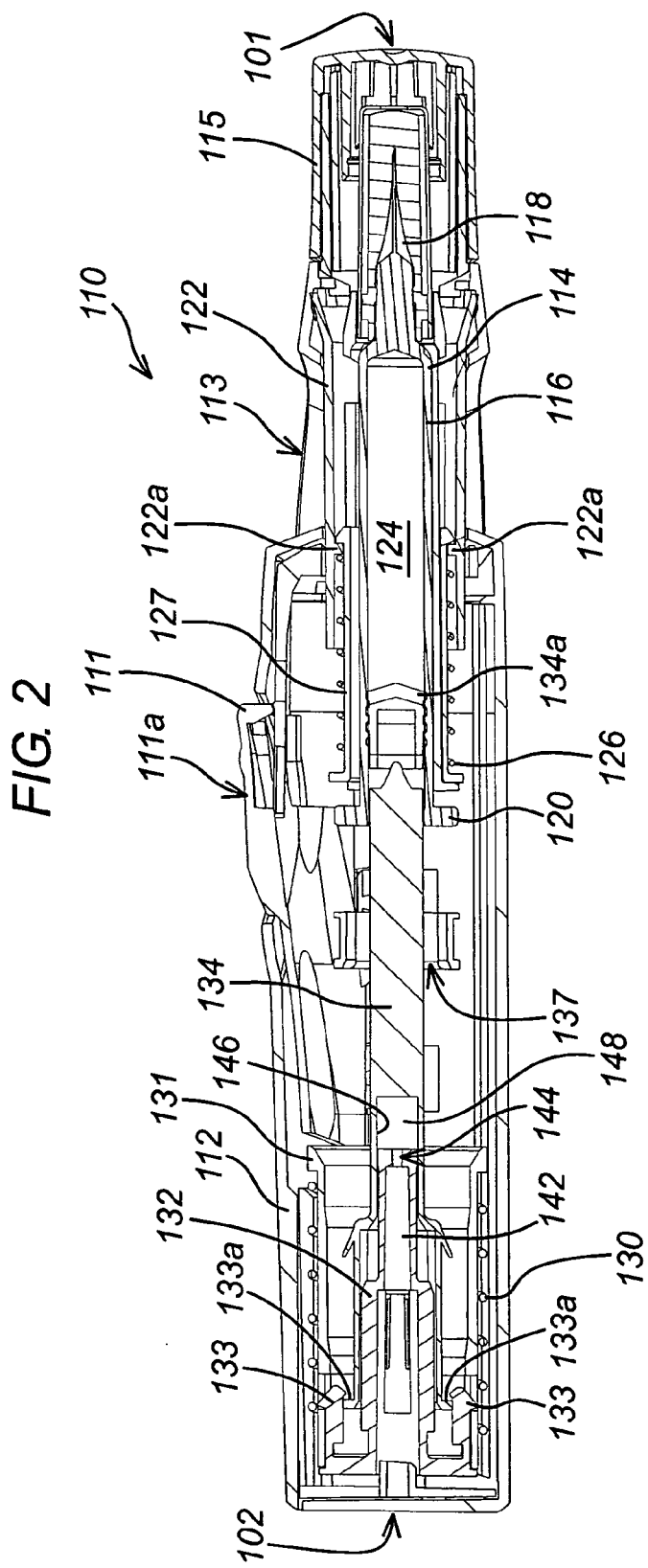
FIG. 2 shows in section the injection device of FIG. 1 before actuation.

FIG. 2 shows the housing 112 containing a hypodermic syringe 114 of conventional type, including a syringe body 116 terminating at one end in a hypodermic needle 118 and at the other in a flange 120. The conventional plunger and bung that would normally be used to discharge the contents of the syringe 114 manually have been removed and replaced with a drive element 134 which includes a bung 134a. This drive element 134 constrains a drug 124 to be administered within the syringe body 116. Whilst the syringe illustrated is of hypodermic type, this need not necessarily be so. Transcutaneous or ballistic dermal and subcutaneous syringes may also be used with the injection device of the present invention. As illustrated, the housing includes a return drive which here takes the form of a compression return spring 126 that biases the syringe 114 from an extended position in which the needle 118 extends from an aperture 128 in the housing 112 to a retracted position in which the discharge nozzle 118 is contained within the housing 112.

The housing 112 includes a support member which, as shown in FIG. 2, takes the form of a cylindrical insert 122. The cylindrical insert 122 has, on its inner surface, a support surface 122a which connects with one end of the return spring 126. The other end of the return spring 126 acts on the syringe 114 via a syringe carrier 127. The support surface 122a is provided, as shown in FIG. 2, by a rim on the inner surface of the cylindrical insert 122. The support surface 122a is positioned beyond the indicator opening 113 away from the proximal end 101 of the housing 112. The return spring 126 connects with the support surface 122a on its end which is located away from the proximal end 101 of the housing 112 and its other end acts on the syringe carrier 127 beyond the support surface 122a from the proximal end 101 of the housing 112. This way, the return spring 126, which surrounds the syringe 114 and syringe carrier 127, cannot be seen through the indicator opening 113 at any time before, during or after triggering of the injection device 110. The cylindrical insert 122 forms a window in the indicator opening 113 formed from transparent material so that the contents of the syringe 114 can be viewed through the indicator opening 113.

At the other end of the housing 112 is a forward drive, which here takes the form of a compression drive spring 130. Drive from the drive spring 130 is transmitted via a multi-component drive to the syringe 114 to advance it from its retracted position to its extended position and discharge its contents through the needle 118. The drive accomplishes this task by acting directly on the drug 124 and the syringe 114. Static friction between the drive element 134 and the syringe body 116 initially ensures that they advance together, until the return spring 126 bottoms out or the syringe body 116 meets some other obstruction (not shown) that retards its motion.

The multi-component drive between the drive spring 130 and the syringe 114 consists of three principal components. A drive sleeve 131 takes drive from the drive spring 130 and transmits it to a first drive element 132. This in turn transmits drive via a damping fluid to a second drive element, the drive element 134 already mentioned.

The first drive element 132 includes a hollow stem 140, the inner cavity of which forms a collection chamber 142 in communication with a vent 144 that extends from the collection chamber through the end of the stem 140. The second drive element 134 includes a blind bore 146 that is open at one end to receive the stem 140 and closed at the other. As can be seen, the bore 146 and the stem 140 defining a fluid reservoir 148, within which the damping fluid is contained.

The trigger 111, when operated, serves to decouple the drive sleeve 131 from the housing 112, allowing it to move relative to the housing 112 under the influence of the drive spring 130. The operation of the device is then as follows.

Initially, the drive spring 130 moves the drive sleeve 131, the drive sleeve 131 moves the first drive element 132 and the first drive element 132 moves the second drive element 134. The second drive element 134 moves and, by virtue of static friction and hydrostatic forces acting through the drug 124 to be administered, moves the syringe body 116 against the action of the return spring 126. The return spring 126 compresses and the hypodermic needle 118 emerges from the exit aperture 128 (not shown) of the housing 112. This continues until the return spring 126 bottoms out or the syringe body 116 meets some other obstruction (not shown) that retards its motion. Because the static friction between the second drive element 134 and the syringe body 116 and the hydrostatic forces acting through the drug 124 to be administered are not sufficient to resist the full drive force developed by the drive spring 130, at this point the second drive element 134 begins to move within the syringe body 116 and the drug 124 begins to be discharged. Dynamic friction between the second drive element 134 and the syringe body 116 and hydrostatic and hydrodynamic forces now acting through the drug 124 to be administered are, however, sufficient to retain the return spring 126 in its compressed state, so the hypodermic needle 118 remains extended.

Before the second drive element 134 reaches the end of its travel within the syringe body 116, so before the contents of the syringe have fully discharged, protrusions (not shown) on the first drive element 132 reach a constriction 137 within the housing 112. The constriction 137 moves the protrusions inwards so that the first drive element 136 is no longer coupled to the second drive element 134. Once this happens, the first drive element 136 no longer acts on the second drive element 134, allowing the first drive element 132 to move relative to the second drive element 134.

Because the damping fluid is contained within a reservoir 148 defined between the end of the first drive element 132 and the blind bore 146 in the second drive element 134, the volume of the reservoir 146 will tend to decrease as the first drive element 132 moves relative to the second drive element 134 when the former is acted upon by the drive spring 130. As the reservoir 148 collapses, damping fluid is forced through the vent 144 into the collection chamber 142. After release of the drive spring 130, some of the force exerted by the drive spring 130 does work on the damping fluid, causing it to flow though the constriction formed by the vent 144; the remainder acts hydrostatically through the fluid and through friction between the first and second drive elements 132, 134, thence via the second drive element 134. Losses associated with the flow of the damping fluid do not attenuate the force acting on the body of the syringe to a great extent. Thus, the return spring 126 remains compressed and the hypodermic needle remains extended.

After a time, the second drive element 134 completes its travel within the syringe body 116 and can go no further. At this point, the contents of the syringe 114 are completely discharged and the force exerted by the drive spring 130 acts to retain the second drive element 134 in its terminal position and to continue to cause the damping fluid to flow though the vent 144, allowing the first drive element 132 to continue its movement.

Before the reservoir 148 of fluid is exhausted, flexible latch arms 133 linking the drive sleeve 131 with the first drive element 132 are no longer forced to engage the drive sleeve 131 by protrusions 133a on the second drive element 134. Once this happens, the drive sleeve 131 acts no longer on the first drive element 132, allowing them to move relative to each other. At this point, of course, the syringe 114 is released, because the forces developed by the drive spring 130 are no longer being transmitted to the syringe 114, and the only force acting on the syringe will be the return force from the return spring 126. Thus, the syringe 114 is now returned to its retracted position and the injection cycle is complete.

All this takes place, of course, only once the cap 115 has been removed from the end of the housing 112. As can be seen from FIG. 2, the end of the syringe 114 is sealed with a boot 123.

Figure 3:
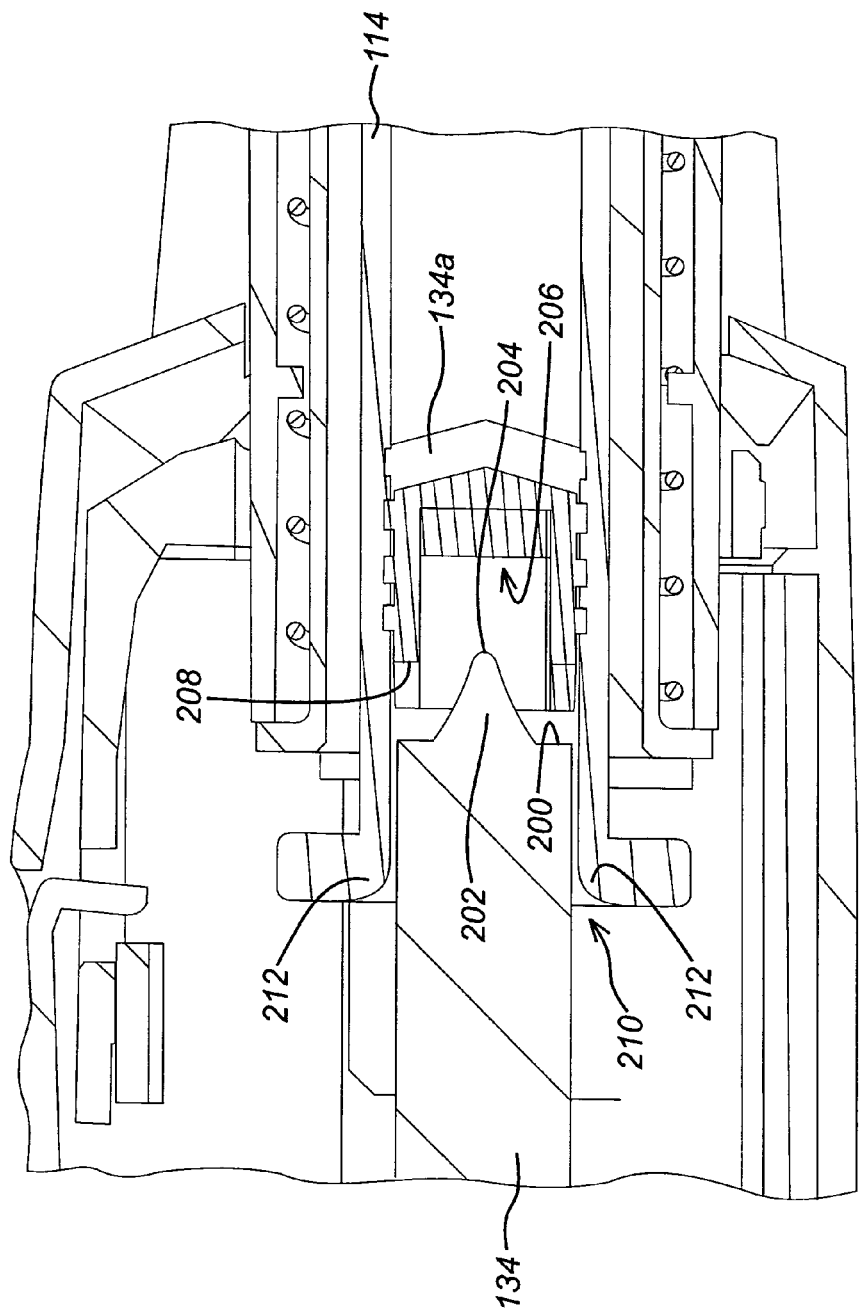
FIG. 3 shows an enlarged portion of FIG. 2.
Figure 4:
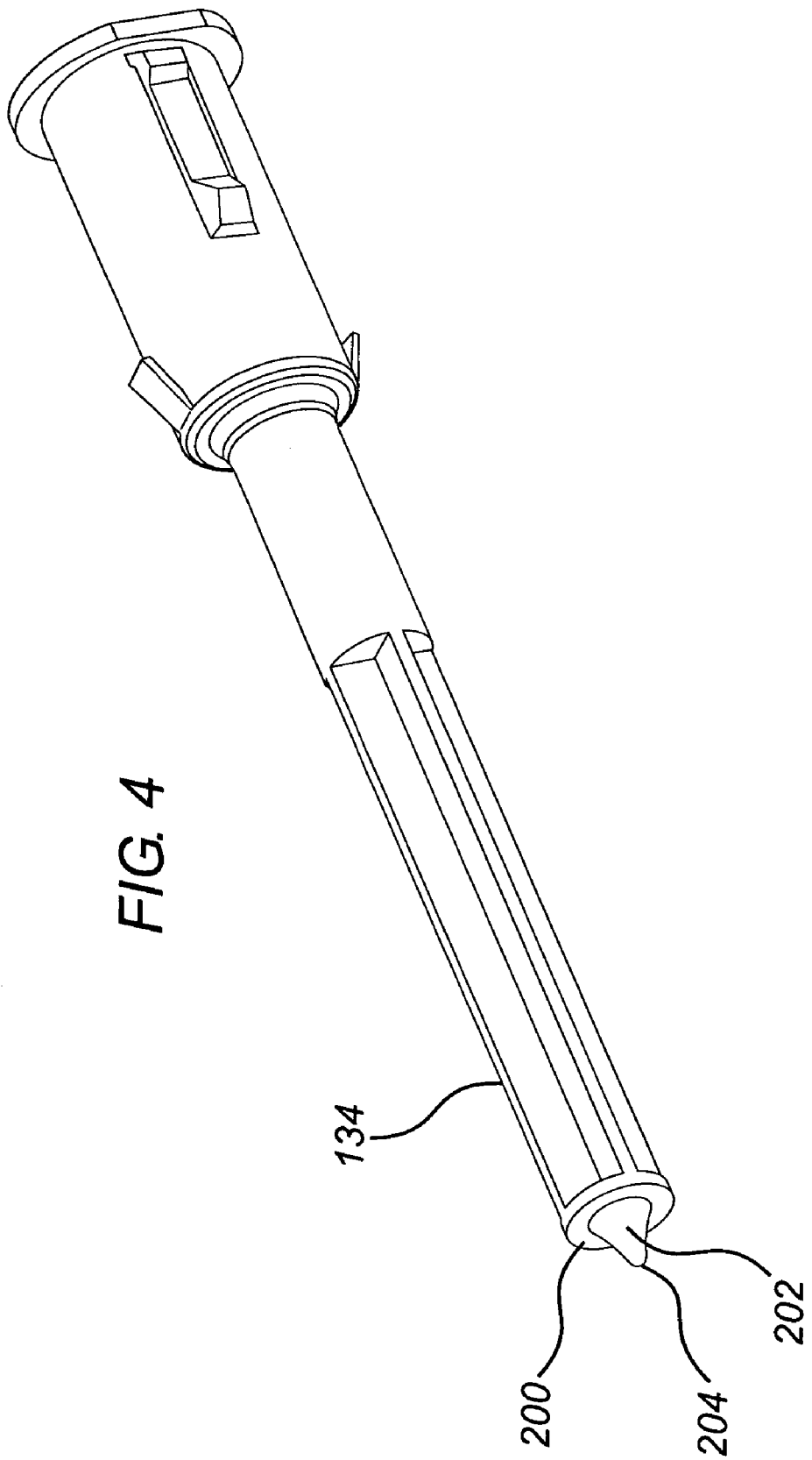
FIG. 4 is a perspective view of the drive element of FIGS. 1-3.

As discussed above and illustrated in FIGS. 3 and 4, the drive element 134 terminates at its forward end in a flat annular region 200 that surrounds a substantially conical middle region 202 terminating in a neb 204. The rubber bung 134a possesses a central bore 206 in which the conical middle region 202 and the neb 204 are received and a skirt 208 that is borne upon by the annular flat region of the end of the drive element 134. The opening 210 in the rear of the glass syringe is flared, in this case by being provided with a radius at region 212. This radius is provided around the whole of the syringe bore opening and thus forms a surface of revolution.

The combination of the radius at regions 212 of the opening 210 to the syringe bore and the projecting conical middle region 202 and the neb 204 of the drive element allows misalignments of the two to be managed. This is because the conical middle region 202 and the neb 204 either pass straight into the opening 210 of the syringe, or contact the radius at regions 212, which guides them towards the centre of the syringe bore. The radius at regions 212 and the substantially flat annular region and the central conical portion 202 and neb 204 of the drive element 134 are so shaped and dimensioned that axial misalignment between the syringe 114 and the drive element 134 during assembly of the injection device are corrected by, firstly, the conical middle region 202 of the drive element riding up the radius at region 212 to a point at which, secondly, the substantially flat annular region 200 of the drive element 134 also makes contact with and rides up the radius at region 212, to align the drive element 134 in the bore of the syringe 114.

In this preferred embodiment of the invention, the inner diameter of the bore of the syringe 114 is 6.35±0.1 mm. The appropriate radius to be provided at regions 212 depends a number of variables. A typical radius may be between 33% and 100% of the radius of the syringe bore; in this preferred embodiment, it possesses a radius of curvature of between 1 mm and 3 mm. Since in this embodiment, the shape and dimensions of the flared opening in the syringe and the substantially flat annular and conical middle regions of the drive element 134 are designed to correct axial misalignment in full, this radius of curvature should preferably be greater than the maximum radial extent of the substantially flat annular region of the drive element 134. Better results are obtained if it is at least 50% greater than the maximum radial extent of the substantially flat edge region of the forward end of the drive element. Even better results follow if it is at least 70% greater. In this embodiment, a radius of 2 mm is preferred, which compares with a maximum radial extent of the substantially flat annular region 200 of the drive element 134 of about 1.15 mm.

The drive element 134 itself has a diameter at its forward of 5.9±0.22 mm (i.e. ±4%) and thus its cross-sectional area is 27.3 mm$^2$±8%. The diameter of the base of the conical middle portion 202 is 3.6 mm±4%, which accounts for about 63% of the total area of the end of the drive element 134; the remaining 37% is accounted for by the flat annular region 200. The conical middle region of the forward end of the drive element has an included cone angle of 65±5°, which means that the sides of the cone taper at about 32.5° from the longitudinal axis of the drive element 134. These various preferred dimensions and angles make up a device that has been found to work extremely well.

A drive element 134 shaped in the way described has further advantages. If it is desired to reduce the dose volume of the device, this is easily done by inserting, during the assembly operation, an additional drive element between element 134 and the bung 134a. At its forward end, the additional drive element should reproduce exactly the shape and dimensions of the drive element 134; at its rearward end, it should reproduce the shape and dimensions of the bore and skirt of the bung 134a. Thus, to the drive element 134, the additional drive element will be indistinguishable from the bung 134a; to the bung 134a, it will be indistinguishable from the drive element 134.

The invention claimed is:

1. An injection device comprising:
a housing having a trigger projecting though the housing;
a hypodermic syringe, including a syringe body terminating at one end in a hypodermic needle, said hypodermic syringe received within the housing, the syringe having a bore terminating at a forward end in a discharge nozzle and at a rearward end in a flared opening in which a discharge piston having a bore at a rearward end portion thereof is inserted;
a drive element having a forward end consisting of a substantially flat edge region that is adapted to bear upon the rearward end of the discharge piston of the syringe and surrounds a projecting middle region which continuously tapers from the substantially flat edge region to a closed end neb and that is adapted to be received in the bore at the rearward end portion of the discharge piston; and
an actuator a drive spring actuatable by the trigger for advancing the syringe from a refracted position in which the discharge nozzle is contained within the housing to an extended position in which the discharge nozzle extends from an aperture in the housing and for advancing the drive element so as to advance the discharge piston and discharge the contents of the syringe through the discharge nozzle.

2. An injection device according to claim 1 in which the flared opening in the syringe and the substantially flat edge and projecting middle regions of the forward end of the drive element are so shaped and dimensioned that axial misalignment between the syringe and the drive element during assembly of the injection device are corrected by, firstly, the projecting middle region of the forward end of the drive element riding up the flared opening of the syringe to a point at which, secondly, the substantially flat edge region of the forward end of the drive element rides up the flared opening of the syringe to align the drive element in the bore of the syringe.

3. An injection device according to claim 2 in which the line formed by the intersection of the flared opening of the syringe and a plane that passes through the axis of the syringe bore possesses a radius of curvature of between 33% and 100% of the radius of the syringe bore.

4. An injection device according to claim 2 in which the line formed by the intersection of the flared opening of the syringe and a plane that passes through the axis of the syringe bore possesses a radius of curvature of between 1 mm and 3 mm.

5. An injection device according to claim 3 in which the said radius of curvature is an average radius of curvature.

6. An injection device according to claim 3 in which the said radius of curvature is a minimum radius of curvature.

7. An injection device according to claim 3 in which the said radius of curvature is greater than the maximum radial extent of the substantially flat edge region of the forward end of the drive element.

8. An injection device according to claim 7 in which the said radius of curvature is at least 50% greater than the maximum radial extent of the substantially flat edge region of the forward end of the drive element.

9. An injection device according to claim 7 in which the said radius of curvature is at least 70% greater than the maximum radial extent of the substantially flat edge region of the forward end of the drive element.

10. An injection device according to claim 1 in which the flared opening of the syringe is substantially a surface of revolution about the axis of the syringe bore.

11. An injection device comprising:
a housing having a trigger projecting through the housing, said housing adapted to receive a hypodermic syringe, including a syringe body terminating at one end in a hypodermic needle, said hypodermic syringe having a bore terminating at a forward end in a discharge nozzle and at a rearward end in a flared opening in which a discharge piston having a bore at a rearward end portion thereof is inserted; and
a drive element that is adapted to bear upon the rearward end of the discharge piston of the syringe; and
an actuator a drive spring actuatable by the trigger for advancing the syringe from a refracted position in which the discharge nozzle is contained within the housing to an extended position in which the discharge nozzle extends from an aperture in the housing for advancing the drive element so as to advance the discharge piston and discharge the contents of the syringe through the discharge nozzle, the forward end of the drive element consisting of a substantially flat edge region surrounding a projecting middle region which continuously tapers from the substantially flat edge region to a closed end neb and that is adapted to be received in the bore at the rearward end portion of the discharge piston.

12. An injection device according to claim 11 in which the forward end of the drive element has a cross-sectional area in the range 6.5 mm$^2$ to 110 mm$^2$.

13. An injection device according to claim 12 in which the forward end of the drive element has a cross-sectional area of 27.3 mm$^2$±8%.

14. An injection device according to claim 11 in which the forward end of the drive element is substantially circular in cross-section.

15. An injection device according to claim 14 in which the forward end of the drive element has a radius in the range 1.45 mm to 5.9 mm.

16. An injection device according to claim 15 in which the forward end of the drive element has a radius of 2.95 mm±4%.

17. An injection device according to claim 11 in which the substantially flat edge region of the forward end of the drive element accounts for between 25% and 50% of the total area of the forward end of the drive element.

18. An injection device according to claim 17 in which the substantially flat edge region of the forward end of the drive element accounts for 37±3% of the total area of the forward end of the drive element.

19. An injection device according to claim 11 in which the substantially flat edge region of the forward end of the drive element is substantially annular.

20. An injection device according to claim 19 in which the inner diameter of the substantially flat annular region is 61±2% of the outer diameter.

21. An injection device according to claim 11 in which the projecting middle region of the forward end of the drive element is substantially circular in shape.

22. An injection device according to claim 11 in which the projecting middle region of the forward end of the drive element tapers at an average angle of between 35±10° to the longitudinal axis of the drive element.

23. An injection device according to claim 11 in which the projecting middle region of the forward end of the drive element is substantially conical or frustoconical.

24. An injection device according to claim 23 in which the conical or frustoconical region of the forward end of the drive element has an included cone angle of 65±5°.

* * * * *